United States Patent [19]

Fischer

[11] Patent Number: Plant 5,534

[45] Date of Patent: Aug. 13, 1985

[54] AFRICAN VIOLET PLANT NAMED SUGAR PLUM

[75] Inventor: Arnold Fischer, Hanover, Fed. Rep. of Germany

[73] Assignee: Pan American Plant Company, Parrish, Fla.

[21] Appl. No.: 539,803

[22] Filed: Oct. 7, 1983

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet named Sugar Plum, particularly characterized by its floriferous, continuous blooming flower habit, two-toned lavender flower color, with the top two petals being darker than the lower three, with each flower being edged in white, and its compact rosette bouquet on erect peduncles above the dark green foliage.

1 Drawing Figure

The present invention comprises a new and distinct cultivar of African violet plant, botanically known as *Saintpaulia ionantha,* and hereinafter referred to by the cultivar name Sugar Plum.

The new cultivar was referred to during the breeding and selection process by the designation V7-H19-N, and is a product of a planned breeding program. The basic objective of the breeding program was to create a new african violet cultivar having novelty type two-toned lavender flowers with a geneva edge and floriferous habit.

The new cultivar was originated from a cross made by Arnold Fischer in a controlled breeding program in Hannover, Germany in 1976. The male and female parents are unknown at this time.

Sugar Plum was discovered and selected by Arnold Fischer as a flowering plant within the progeny of the stated cross in a controlled environment in Fallbrook, Calif. in 1977. Asexual reproduction of the new cultivar by leaf cuttings, as performed by me at West Chicago, Ill., and Parrish, Fla., has demonstrated that the combination of characteristics as herein disclosed for the new cultivar are firmly fixed and retained through successive generations of asexual reproduction.

Sugar Plum has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Sugar Plum, which in combination distinguish this African violet as a new and distinct cultivar:

1. Two-toned lavender flower color, with the top two petals being darker than the lower three (zygomorphic rotate).
2. White geneva edge around each flower.
3. Compact rosette habit with flowers on erect upright peduncles.
4. Suitable for production in 10 cm. pots, flowering in 9 to 13 weeks depending upon growing conditions.
5. Very floriferous, with flowers continuing to open for many weeks after onset of flowering.

6. Dark green, pubescent foliage with a slightly crenate leaf margin.

The new cultivar is most similar to Aurora, a cultivar of applicant disclosed in U.S. Plant Pat. No. 4,972. Sugar Plum is principally distinguished from Aurora by its smaller, darker green foliage, more floriferous nature and two-tone lavendar blossoms, where Aurora is solid dark blue. Both display a white picatee.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under 5000 foot candles of natural light at approximately 11:30 A.M. in Parrish, Fla.

Parentage:

*Male parent.*—Unknown.

*Female parent.*—Unknown.

Propagation: The new cultivar holds its distinguishing characteristics through successive propagations by leaf cuttings.

Plant: From 4 cm. to 8 cm. tall when grown in pots, and approximately 22 cm. in diameter when fully grown. The growth rate is vigorous, and the general shape of the fully grown plant is round.

*Leaves.*—Quantity: Abundant. Shape: Cordate with crenate margin. Diameter: 45–65 mm. Texture: Pubescent, glossy. Ribs and veins: Pinnate. Color (upperside): 147A. Color (Underside): Veins 186A; mid-rib and portions of veins 147D with some purple. Peticles: 2–7 cm. in length.

*Flowers.*—Buds: Size: Up to 8 mm.×8 mm. Shape: Round. Rate of opening: Normal. Sepals: Shape: Lanceolate. Color: 183B with show of 147D. Phyllaries: Two; lanceolate. Color: 147B. Calyx: Shape: Funnel. Size: About 10 mm. diameter. Aspect: Hairy. Peduncle: Length: 30–60 mm. Character: Erect and rigid. Individual Flowers: Number of petals: Five (5). Size 30–55 mm. in diameter, 7 mm. deep. Shape: Cup-shaped when bloom first opens, becoming flat as bloom matures. Color: Upperside; Top two petals 83A approaching 82B near edges; bottom three petals 82B approaching 83B toward center. Underside: 81C and 81D. Flowers fade slightly as they age. Flower color varies with amount of light, temperature, fertilizer, and other growing conditions. Borne: In a cyme on 35–55 mm. peduncles. Flowering habit: Flowers profusely and intermittently year round, with blooms lasting 2–3 weeks after which petals dry up but do not drop. Finishes in 9–13 weeks when a 2¼" plantlet is placed in a 10 cm. pot.

*Reproductive organs.*—Stamens: Stamens borne singly on one side of ovary, 2 anthers, basifix. Anthers: 2 mm.×2 mm., yellow. Filaments: 2–3 mm., lavender-yellow. Pollen Color: Yellow. Pistels: Number: One. Styles: One, 5–6 mm. long, color-77A. Stigma: Sticky, white. Ovaries: Superior.

*Roots.*—Fiberous and fine.

*Disease resistance.*—No African violet diseases observed to date.

General observations: The flowers of Sugar Plum are held aloft on erect peduncles above the dark green foliage to form a massive colorful bouquet. The single zygomorphic rotate flower bears 5 petals, the three bottom petals being larger and lighter in color than the top two petals. All petals are edged ever so slightly in white. It may be finished in 9–13 weeks from a 2¼" plant in a 10 cm. pot in a controlled environment.

I claim:

1. A new and distinct cultivar of African violet named Sugar Plum, as described and illustrated, and particularly characterized by its floriferous, continuous blooming flower habit; two-toned lavender flower color, with the top two petals being darker than the lower three, with each flower being edged in white, and its compact rosette bouquet on erect peduncles above dark green foliage.

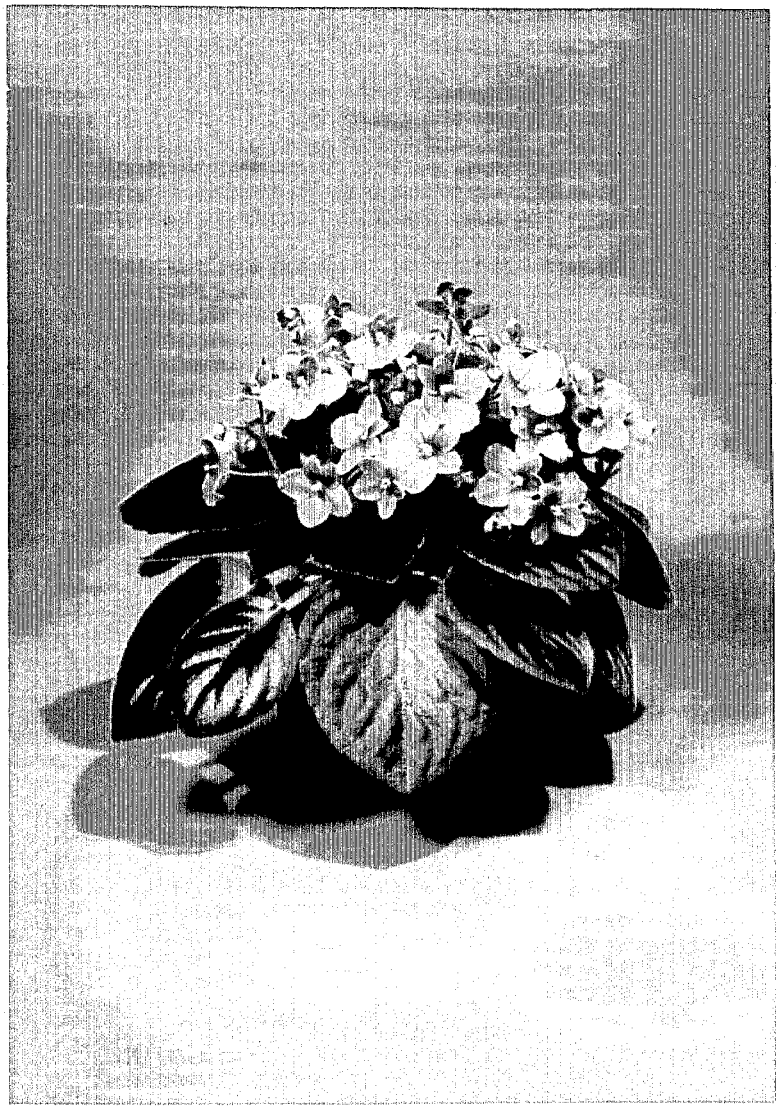

* * * * *